United States Patent
Rauchschwalbe et al.

(10) Patent No.: US 6,787,666 B2
(45) Date of Patent: Sep. 7, 2004

(54) PROCESS FOR THE PREPARATION OF ISOLATED 3,4-DIAMINOBENZENESULPHONIC ACID

(75) Inventors: Günter Rauchschwalbe, Leverkusen (DE); Herbert Emde, Köln (DE); Wolfram Kissener, Neunkirchen-Seelscheid (DE)

(73) Assignee: Bayer Chemicals AG, Leverkusen (DE)

( * ) Notice: Subject to any disclaimer, the term of this patent is extended or adjusted under 35 U.S.C. 154(b) by 0 days.

(21) Appl. No.: 10/663,827

(22) Filed: Sep. 16, 2003

(65) Prior Publication Data

US 2004/0059126 A1 Mar. 25, 2004

(30) Foreign Application Priority Data

Sep. 17, 2002 (DE) ........................................ 102 43 028

(51) Int. Cl.$^7$ ............................................ C07C 309/00
(52) U.S. Cl. ...................................................... 562/58
(58) Field of Search ........................................... 562/58

(56) References Cited

U.S. PATENT DOCUMENTS

| | | | |
|---|---|---|---|
| 4,435,336 A | * 3/1984 | Emde et al. | 562/68 |
| 4,808,342 A | * 2/1989 | Lund et al. | 562/58 |
| 4,968,835 A | * 11/1990 | Blank et al. | 562/58 |
| 5,473,079 A | 12/1995 | Heywang et al. | 548/305.4 |
| 6,440,401 B1 | 8/2002 | Heywang et al. | 424/59 |
| 6,593,476 B2 | 7/2003 | Heywang et al. | 548/310.7 |
| 2002/0013474 A1 | 1/2002 | Heywang et al. | 548/304.4 |
| 2002/0016349 A1 | 2/2002 | Heywang et al. | 514/394 |

FOREIGN PATENT DOCUMENTS

DE 2131367 12/1972

OTHER PUBLICATIONS

J. Post, Liebigs Ann. Chemie 205, (month unavailable) (1880), "Ueber die Einwirkung der Schwefelsäure auf substituirte Nitro– und Amidobenzole" pp. 33–112.

Zincke and Kuchenbecker, Ann. 330, (month unavailable) (1904), Justus Liebig's Annalen der Chemie. "Ueber die Einwirkung von Chlorkalk auf Diazo– und Isodiazoverbindungen" pp. 1–37.

R. Nietzki und Zd. Lerch: Ueber Orthonitranilinsulfosäure und einige daraus dargestellte Verbindungen. Ber. d. deutsch. Chem. Ges. 21, 3220 (1888) 4 pages.

Patent Abstracts of Japan Bd. 006, Nr. 122, Jul. 7, 1982 & JP 57 048961 A (Sumitomo Chem Co Ltd), Mar. 20, 1982 (Mar. 2, 1982) "Zusammenfassung".

Patent Abstracts of Japan Bd. 006, Nr. 122, 7 . Jul. 7, 1982 & JP 57 048961 A (Sumitomo Chem Co LtD), Mar. 20, 1982 "Zusammenfassung".

* cited by examiner

*Primary Examiner*—Fiona T. Powers
(74) *Attorney, Agent, or Firm*—Godfried R. Akorli; Diderico van Eyl; Jill Deneavich

(57) ABSTRACT

Described herein is a process for the preparation of 3,4-diaminobenzenesulphonic acid, characterized in that 1,2-diaminobenzene is reacted with anhydrous sulphuric acid which optionally comprises $SO_3$ in up to stoichiometric amount, at a temperature in the range from 100 to 160° C. with stirring for a reaction time of from 1 to 20 hours; water or ice is added to the reaction mixture, optionally with cooling, up to a sulphuric acid concentration in the range from 30 to 75% by weight, based on the total mixture; the 3,4-diaminobenzenesulphonic acid precipitated out of the reaction mixture is filtered off, optionally washed with dilute sulphuric acid and worked up.

5 Claims, No Drawings

PROCESS FOR THE PREPARATION OF ISOLATED 3,4-DIAMINOBENZENESULPHONIC ACID

BACKGROUND OF THE INVENTION

1. Field of the Invention

The invention relates to a process for the preparation of 3,4-diaminobenzenesulphonic acid by sulphonation of 1,2-diaminobenzene with sulphuric acid which contains no $SO_3$ or only up to 1.0 mol of $SO_3$ per mole.

2. Brief Description of the Prior Art

The objective of the invention is to provide a simple process for the preparation of 3,4-diaminobenzenesulphonic acid (also called "orthaminic acid") which is particularly useful as an intermediate product. Illustratively, this compound is useful as an intermediate for the preparation of dyes, crop protection compositions, pharmaceutical products, and cosmetic products, particularly of UV absorbents in light protection agents such as 2-phenylbenzimidazolemonosulphonic acid. Particularly pure products are required for the last-mentioned intended use in particular, since the end products should be pure white. The prior art processes for preparing the compounds and the associated disadvantages are described hereunder.

In accordance with the prior art, 3,4-Diaminobenzenesulphonic acid can be obtained, by reacting the HCl salt of 1,2-diaminobenzene with a large excess (about 11 mol/mol) of $SO_3$-containing sulphuric acid (see J. Post, Liebigs Ann. Chemie 205 (1880), p. 100).

However, the use of the HCl salt leads to the evolution of considerable amounts of HCl gas, which has a corrosive action, requires the use of sealed apparatuses made of expensive materials and would hinder reuse of the sulphuric acid.

Moreover, it has hitherto not been possible to obtain orthaminic acid as isolated product from a sulphonation of free 1,2-diaminobenzene with excess sulphuric acid. Thus, it is necessary to precipitate out the entire excess of $H_2SO_4$ with $BaCl_2$ and evaporate the mother liquor which remains. The product obtained in this way does not readily crystallize and has to be purified again, which is laborious.

For the isolation, aromatic sulphonic acids are often converted into Na salts, which are then less readily soluble than the pure sulphonic acid. Incidentally, this is not known of orthaminic acid.

A further possible route for the synthesis of orthaminic acid is the reduction of 2-nitroaniline-4-sulphonic acid or dinitroazobenzenedisulphonic acid with tin/HCl (Zincke and Kuchenbecker, Ann. 330, (1904), p. 23). However, these starting materials are not inexpensive and have to be synthesized via several stages. Orthaminic acid is obtained in the process as HCl salt, which decomposes readily (Nietzki, Lerch; Ber. d. deutsch. Chem. Ges. 21, 3220 (1888)). Also the orthaminic acid obtained by this route is impure, and darkly discolored, as such purification by recrystallization is necessary (loc.cit.). Moreover, since HCl is highly corrosive, the handling of acidic, decomposable HCl salts is therefore not preferred on an industrial scale.

The synthesis by sulphonation of 1,2-diaminobenzene would, by contrast, be advantageous since 1,2-diaminobenzene is obtainable in considerable amounts. In this synthesis it is desirable to isolate intermediates if they are to be obtained in the purest possible form and further processed.

Without intermediate isolation which (apart from starting materials and secondary products) can, as in this case, still comprise large amounts of sulphuric acid, it is not always possible to further process crude reaction solutions. This often leads to the formation of contaminated products and/or to poor yields in the subsequent stage. This is described in the example in EP-A 4 203 072, wherein a mixture of 1,2-diaminobenzene, benzoic acid and 96% strength sulphuric acid is mixed and heated to 200° C. In the subject process, 2-phenylbenzimidazole-5-sulphonic acid is obtained as the secondary product in a yield of 49% of theory. The product is isolated in a yield of 60%, with the process carried out in 86% strength sulphuric acid at 178°.

However, the formation or even isolation of orthaminic acid by this route is not described; the process, which is carried out with aqueous sulphuric acid and a particularly high temperature, does not therefore suggest the process according to the invention. In fact, the increase in the yield with increasing water content of the sulphuric acid in the examples described teaches away from the use of 100% strength or $SO_3$-containing sulphuric acid.

Similarly EP-A 1167358 and EP-A 1167359 via the examples show that in the reaction of benzoic acid, 1,2-diaminobenzene and sulphuric acid in the presence of considerable amounts of $SO_3$ at a processing temperature of about 120°, considerable amounts of the disulphonic acids of 2-phenylbenzimidazole are obtained, even exclusively.

An intermediate isolation of orthaminic acid which has been obtained by sulphonation is nowadays highly desirable and required for the following economic and ecological reasons: Since the sulphonation is carried out in an excess of sulphuric acid (see J. Post, loc. cit.), contaminated sulphuric acid is formed in the process, the reutilization of which is desired. Spent sulphuric acid is nowadays either concentrated with oxidation of organic ingredients, or cleaved back at a high temperature to give $SO_2$ in order to be converted again into pure ready-to-use sulphuric acid. For this, the desired material-of-value must of course be largely removed beforehand, and contamination with inorganic ions (as in the precipitation of the sulphonic acid as e.g. Na or K salt) is unacceptable since that would lead to problems in the work-up.

Furthermore, it has been found that during the sulphonation of 1,2-diaminobenzene in sulphuric acid which comprises a super-stoichiometric amount of $SO_3$, considerable amounts of disulphonic acid are produced.

It was therefore the object to find a way of preparing orthaminic acid by reacting 1,2-diaminobenzene with sulphuric acid and isolating it therefrom in the purest possible form, in a high yield and free from inorganic cations such that the sulphuric acid used can be reused and orthaminic acid can be obtained therefrom in a high purity and yield.

SUMMARY OF THE INVENTION

Surprisingly, it was then possible to find conditions to sulphonate 1,2-diaminobenzene with anhydrous sulphuric acid which comprises no $SO_3$ or only up to 1.0 mol of $SO_3$ per mole, and to work up the sulphonation mixture such that 3,4-diaminobenzenesulphonic acid is obtained in high yield and high purity, and that the separated-off sulphuric acid is free from inorganic cations which would impair reutilization.

This is particularly surprising since under otherwise identical conditions it was not possible to react the structurally very similar 1,3-diaminobenzene to give 1,3-diaminobenzenesulphonic acid such that it could be correspondingly isolated from the sulphonation mixture. In this case, the conversion achieves only about 50%.

The invention therefore provides a process for the preparation of 3,4-diaminobenzenesulphonic acid, characterized in that
a) 1,2-diaminobenzene is reacted with anhydrous sulphuric acid which optionally comprises $SO_3$ in up to stoichiometric amount, at a temperature in the range from 100 to 160° C. with stirring for a reaction time of from 1 to 20 hours,
b) water or ice is added to the reaction mixture, optionally with cooling, up to a sulphuric acid concentration in the range from 30 to 75% by weight, based on the total mixture,
c) the 3,4-diaminobenzenesulphonic acid precipitated out of the reaction mixture is filtered off, optionally washed with dilute sulphuric acid and worked up.

The product obtained by said process does not, in contrast to earlier findings about products of a different origin, decompose, but is stable.

The product which is obtained by this process is white to dark grey, generally pale grey. This is particularly surprising since 1,2-diaminobenzene is readily oxidizable and sulphuric acid acts as a strong oxidizing agent particularly at elevated temperature. It was therefore to be expected that the sulphonation would take place in parallel to oxidation and the formation of considerable amounts of darkly coloured secondary products, which would have automatically lead to a poor yield.

DETAILED DESCRIPTION OF THE INVENTION

In accordance with the process of the invention, 1,2-diaminobenzene is introduced into an excess of 100% strength sulphuric acid or an excess of $SO_3$-containing sulphuric acid (but in an amount of $SO_3$ which is below 1 mol per mole of phenylenediamine), heated for a few hours, optionally diluted with further sulphuric acid and then diluted with enough water to produce a sulphuric acid of a certain concentration; in the process, orthaminic acid precipitates out in crystalline form in a high yield and can be separated off by suitable measures, such as filtration, centrifugation etc.

A washing with sulphuric acid of a certain dilution is possible, but is generally not required since the product is already produced in high purity (isomerically pure according to 1H-NMR spectrum). This is even more surprising since there are two positions available in the electron-rich aromatic nucleus of the 1,2-diaminobenzene which are very similar in their reactivity, and therefore the formation of comparable amounts of 3,4- and 2,3-diaminobenzenesulphonic acid had been expected. Nevertheless, the yield of isolated product is up to 92–94% of theory of orthaminic acid, based on 1,2-diaminobenzene used (determination by HPLC or nitrite titration), which, according to 1H-NMR spectrum, is obtained in isomerically free form.

Depending on the reaction conditions, 1,2-diaminobenzenedisulphonic acid can form as secondary product (in an amount of a few %); this is separated off during work-up and is virtually not present in the product (content <1.0%).

Depending on the reaction conditions, starting material may also remain unreacted in a small amount; this is separated off during work-up and is no longer present in the product.

If, when an approximately stoichiometric amount of $SO_3$ is used, disulphonic acid is formed to an increased degree, then its fraction can be greatly reduced by adding water after the sulphonation (but before the work-up).

The sulphonation takes place in a temperature range from 90 to 160° C.

In a preferred embodiment, 1,2-diaminobenzene is dissolved in 3–5 times the amount by weight of 100% strength sulphuric acid. (The exact amount is established so that the batch can still be readily stirred or conveyed in the work-up.)

The solution is heated to a temperature of from 100° C. to 160° C.; in a particularly preferred embodiment heated to a temperature of 120–150° and stirred for 1 to 20 hours, in particular 4–15 hours, preferably 6–10 hours.

In a particular embodiment, after the sulphonation reaction has been carried out and prior to the dilution with a large amount of water, a small amount of water is firstly added and the batch is after-stirred for a further 1–3 hours at the processing temperature, during which the already very low content of disulphonic acid can be further reduced.

Then, optionally after cooling to 100° C., the mixture is discharged onto water or ice so that the concentration of the sulphuric acid following dilution is 30 to 75%, preference being given to a concentration of from 40 to 70%, very particular preference being given to a concentration of from 50 to 65%, since, the product then has particularly good filtration properties and is particularly sparingly soluble.

If, during the dilution of the sulphuric acid, the receiver is not cooled, then the product initially remains in solution since the receiver heats up as a result of the heat of dilution. Upon cold stirring, the product then crystallizes out.

In a particular embodiment, sulphuric acid of the desired dilution is initially introduced and, at the desired temperature, both water and the sulphonation mixture are metered in simultaneously such that the concentration of the sulphuric acid (calculated from sulphuric acid and water) in the receiver remains constant.

In the process, it is desirable that the temperature in the receiver is kept low enough for the product to crystallize out during the metered addition.

The precipitated product is then filtered off. It is obtained in sufficiently pure form even without washing, but can be further purified by after-washing with dilute sulphuric acid. The product then still comprises a little adhering sulphuric acid, but this generally does not have to be removed further for the further processing.

The content of desired product can be determined in a simple manner, e.g. by HPLC or diazotization. It is generally 30–50%, in most cases 45–50%, depending on the work-up conditions.

The waste acid which discharges comprises only a little organic material (<about 1% by weight of orthaminic acid and small amounts of disulphonic acid), meaning that it can be reused, optionally after work-up.

The isolated product is, according to 1H-NMR spectroscopy (400 MHz), free from isomers:
(DMSO-d6) δ=6.92 (d, J=8.3 Hz), 7.24 (d/d, J=1.92/8.3 Hz), 7.43 (d, J=1.91 Hz), 8.1 s(broad).

Crude product obtained in this way can therefore be used as it is for many purposes, for example for the preparation of products of pharmaceutical chemistry or of agrochemistry, for dyes or cosmetic products. The invention thus further provides for the use of the 3,4-diaminobenzenesulphonic acid prepared according to the invention for the preparation of products in the pharmaceutical, crop protection, cosmetics or dyes sector.

Optionally, the product can also be recrystallized from, for example, 3 to 5 times the amount by weight of water in order to obtain particularly pure product, e.g. free from $H_2SO_4$.

Product recrystallized in this way gives correct elemental analyses:

| Calc.C: | 38.3% | found C: | 38.0% |
|---|---|---|---|
| Calc.H: | 4.3% | found H: | 4.1% |
| Calc.N: | 14.88% | found N: | 14.8% |
| Calc.S: | 17.03% | found S: | 17.4% |

Content from diazotization: 99.6%

Infrared spectrum:

ν=3454(w), 3364(w), 2873(s,br), 2638(s), 1639(s), 1556 (m), 1502(s), 1316(w) 1230(s), 1207(s), 1168(m), 1145 (s), 1106(s), 1021(s), 819(w).

(s: strong, m: medium, w: weak),

The invention further provides for the use of the 3,4-diaminobenzenesulphonic acid prepared in accordance with the invention for the preparation of products in the pharmaceutical, crop protection, cosmetics and dyes sector.

EXAMPLES

Example 1

600 ml (1110 g) of 100% strength sulphuric acid are initially introduced, 216 g (2.0 mol) of 1,2-diaminobenzene are dissolved therein and the mixture is heated for 2–3 hours at 100° C.

275 g of 65% $SO_3$-containing sulphuric acid are then added dropwise (2.23 mol of $SO_3$) and the mixture is stirred for a further 2 hours at 140° C.

The mixture is cooled to 125° C. and 70 ml of water are added dropwise. The mixture is stirred for a further 2 hours at 135–140° C., cooled to 100° C. and discharged with stirring onto 1300 ml of water over the course of 15 minutes.

The mixture is stirred with cooling to 25° C. over the course of 6 hours and filtered over an acid-resistant filter.

This gives 724 g of 47.6% strength orthaminic acid (91.5% of theory) and 2060 g (1.6 l) of salt-free waste acid which still comprises 0.25% of diaminobenzene and 0.6% of orthaminic acid.

The grey product can be used without further purification.

Example 2

368 g (3.76 mol) of 100% strength sulphuric acid are initially introduced, 48.5 g (0.257 mol) of 1,2-diaminobenzene are dissolved therein and the mixture is heated to 135° C., later to 138° C.:

The reaction is monitored by HPLC (data in rel. mol %)

| Reaction conditions | Starting material | Product (monosulphonic acid) | Secondary product (disulphonic acid) |
|---|---|---|---|
| 6 h/135° | 7.2 | 90.95 | 1.9 |
| 9 h/135° | 6.1 | 92.05 | 1.8 |
| +3 h/138° | 5.7 | 92.37 | 1.9 |
| +3 h/138° | 3.6 | 94.50 | 1.95 |

The mixture is discharged onto 200 g of water and orthaminic acid is isolated, which is obtained in crystalline form (assessment under the microscope at 10 times magnification; yield 96% of theory).

Example 3

The procedure is as in Example 1, but heating is carried out for 8 h at 138° C.

This gives orthaminic acid in a yield of 93.8% of theory.

| Reaction conditions | Starting material | Product | Secondary product |
|---|---|---|---|
| 8 h/138° | 2.8 | 95.4 | 1.7 |
| Isolated product | 0.6 | 98.8 | 0.6 |

Example 4

313 g (3.19 mol) of sulphuric acid are initially introduced, 48.5 g (0.257 mol) of 1,2-diaminobenzene are dissolved therein and the mixture is heated to 138° C.

Later, a further 10 g of sulphuric acid which comprises 65% $SO_3$ (0.08 mol) are added.

The reaction is monitored by HPLC (data in rel. mol %).

The mixture is discharged onto 200 ml of water and cooled to 40°, and the precipitated product is isolated by filtration. This gives orthaminic acid in a yield of 98.1% of theory.

| Reaction conditions | Starting material | Product (orthaminic acid) | Secondary product (disulphonic acid) |
|---|---|---|---|
| 6 h/138° | 4.1 | 91.2 | 2.1 |
| Subsequent addition of oleum and 3 h/138° | 3.1 | 91.9 | 4.0 |
| Isolated product | 0.4 | 98.0 | 1.6 |

Example 5

313 g of sulphuric acid is initially introduced, 48.5 g of 1,2-diaminobenzene are dissolved therein and the mixture is heated for 8 h at 145° C.

The results are monitored by HPLC.

The mixture is discharged onto 220 ml of water and cooled and the product is isolated by filtration.

Orthaminic acid in a yield of 93.8% of theory is isolated.

| Reaction conditions | Starting material | Product (orthaminic acid) | Secondary product (disulphonic acid) |
|---|---|---|---|
| 8 h/145° | 1.9 | 94.3 | 3.8 |
| Isolated product | 1.1 | 98.3 | 0.6 |

Example 6

970 g of 1,2-diaminobenzene (8.965 mol) are dissolved in 3786 ml (7000 g/71.5 mol; 8 mol/mol) of 100% strength sulphuric acid ("monohydrate") and the mixture is heated for 8 hours at 138° C.

The mixture is cooled to 100° C., diluted with 925 g of sulphuric acid and discharged onto 5.05 l of water.

The mixture is cooled to 40° C., giving orthaminic acid with an average content of about 50% (determined by diazotizing and correction by HPLC) in a yield of about 94% of theory.

Example 7

600 g of sulphuric-acid-moist crude orthaminic acid are dissolved in hot 1700 ml of water, stirred with 8 g of activated carbon for 30 minutes at 80°, filtered while hot and stirred until cold.

The precipitated product is filtered off with suction and dried.

This gives 135 g of dry product which, according to HPLC, has a content of 98.8%.

The waste acid which runs off comprises 0.9% orthaminic acid.

Example 8

48.7 g of 1,2-diaminobenzene are dissolved in 249 g/2.53 mol (5.7 mol/mol) of 100% strength sulphuric acid and the mixture is heated. The results are monitored by HPLC.

| Reaction conditions: temperature | Starting material | Product (orthaminic acid) |
|---|---|---|
| 1 h/80° | 96.2 | 2.4 |
| 2 h/80° | 96.1 | 3.3 |
| 2 h/90° | 88.9 | 7.1 |
| 2 h/100° | 83.6 | 12.1 |
| 2 h/110° | 71.6 | 24.8 |
| 2 h/120° | 51.3 | 41.7 |
| 2 h/130° | 15.0 | 84.0 |
| 2 h/140° | 5.5 | 93.3 |

Example 9

49 g of 1,2-diaminobenzene are dissolved in 276 g (2.82 mol; 6.2 mol/mol) of 100% sulphuric acid and the mixture is heated to 135° C.

The reaction results are monitored by HPLC.

| Reaction conditions: time [h] | Starting material | Product (orthaminic acid) | Secondary product (disulphonic acid) |
|---|---|---|---|
| 2 | 27.2 | 69.2 | 3.8 |
| 4 | 14.0 | 81.9 | 4.2 |
| 5 | 10.5 | 86.7 | 2.8 |
| 6 | 8.3 | 88.8 | 2.9 |
| 8 | 6.6 | 90.6 | 2.8 |
| 10 | 5.3 | 92.2 | 2.6 |
| 12 | 6.4 | 91.1 | 2.5 |
| 14 | 5.3 | 92.7 | 2.3 |
| 16 | 4.9 | 93.9 | 2.3 |

Comparative Example 48.5 g of 1,3-diaminobenzene were dissolved in 170 ml of 100% strength sulphuric acid and slowly heated. The conversion was monitored by HPLC. The degree of conversion only reached a maximum of 48 mol % at 140° even after 13 h.

Increasing the temperature to 160° C. increased the conversion after a further 2 hours only to 51%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of 3,4-diaminobenzenesulphonic acid, comprising reacting a) 1,2-diaminobenzene with anhydrous sulphuric acid which optionally comprises $SO_3$ in up to stoichiometric amount, at a temperature in the range from 100 to 160° C. with stirring for a reaction time of from 1 to 20 hours, b) adding water or ice to the reaction mixture, optionally with cooling, up to a sulphuric acid concentration in the range from 30 to 75% by weight, based on the total mixture, c) filtering off the 3,4-diaminobenzenesulphonic acid precipitated out of the reaction mixture, optionally washing it with dilute sulphuric acid, and work-up.

2. Process according to claim 1, characterized in that the 3,4-diaminobenzenesulphonic acid is worked up in hot water by treatment with activated carbon.

3. Process according to claim 1, characterized in that the sulphuric acid or sulphuric acid equivalent is used in a molar ratio of from 5 to 15:1 and $SO_3$ is used in a molar ratio of from 1.5 to 0:1.

4. Process according to claim 1, characterized in that the reaction in step a) is carried out in a temperature range from 120° C. to 150° C.

5. Process according to claim 1, characterized in that the reaction in step a) is carried out in a reaction time of from 5 to 15 hours.

* * * * *